(12) United States Patent
Srivastava et al.

(10) Patent No.: US 9,308,206 B2
(45) Date of Patent: Apr. 12, 2016

(54) COMPOSITIONS AND METHODS FOR TREATING COLON CANCER

(71) Applicants: Satish K Srivastava, Galveston, TX (US); Kota V Ramana, Galveston, TX (US)

(72) Inventors: Satish K Srivastava, Galveston, TX (US); Kota V Ramana, Galveston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 83 days.

(21) Appl. No.: 14/164,459

(22) Filed: Jan. 27, 2014

(65) Prior Publication Data

US 2014/0206693 A1    Jul. 24, 2014

Related U.S. Application Data

(63) Continuation-in-part of application No. 12/586,050, filed on Sep. 16, 2009, now abandoned, which is a continuation-in-part of application No. 11/282,801, filed on Nov. 18, 2005, now Pat. No. 7,702,430, application No. 14/164,459, which is a continuation-in-part of application No. 11/210,283, filed on Aug. 23, 2005, now abandoned, said application No. 12/586,050 is a continuation of application No. 11/478,069, filed on Jun. 29, 2006, now abandoned.

(60) Provisional application No. 60/629,448, filed on Nov. 19, 2004, provisional application No. 60/603,725, filed on Aug. 23, 2004.

(51) Int. Cl.

| | |
|---|---|
| *A61K 38/44* | (2006.01) |
| *A61K 31/517* | (2006.01) |
| *A61K 31/195* | (2006.01) |
| *A61K 31/426* | (2006.01) |
| *A61K 31/4188* | (2006.01) |
| *A61K 31/4747* | (2006.01) |
| *A61K 31/502* | (2006.01) |
| *C12Q 1/26* | (2006.01) |
| *G01N 33/573* | (2006.01) |
| *G01N 33/574* | (2006.01) |
| *A61K 38/00* | (2006.01) |
| *C12N 15/113* | (2010.01) |

(52) U.S. Cl.
CPC ............ *A61K 31/517* (2013.01); *A61K 31/195* (2013.01); *A61K 31/4188* (2013.01); *A61K 31/426* (2013.01); *A61K 31/4747* (2013.01); *A61K 31/502* (2013.01); *C12Q 1/26* (2013.01); *C12Y 101/01021* (2013.01); *G01N 33/5735* (2013.01); *G01N 33/57419* (2013.01); *C12N 15/1137* (2013.01); *C12N 2310/14* (2013.01); *G01N 2500/00* (2013.01)

(58) Field of Classification Search
None
See application file for complete search history.

(56) References Cited

U.S. PATENT DOCUMENTS

| | | | |
|---|---|---|---|
| 5,284,870 | A | 2/1994 | Yoshida |
| 7,702,430 | B2 | 4/2010 | Srivastava |
| 2003/0144308 | A1 | 7/2003 | Bauer et al. |
| 2005/0004225 | A1* | 1/2005 | Balendiran ................. 514/571 |
| 2006/0110814 | A1* | 5/2006 | Srivastava et al. ........... 435/189 |
| 2008/0138437 | A1* | 6/2008 | Sakuma et al. .............. 424/602 |

OTHER PUBLICATIONS

Kang et al. Phorbol ester up-regulates aldose reductase expression in A549 cells: a potential role for aldose reductase in cell cycle modulation. CMLS, Cell. Mol. Life Sci. 62,1146-1155 (2005).

Lee et al. Inhibition of aldose reductase enhances HeLa cell sensitivity to chemotherapeutic drugs and involves activation of extracellular signal-regulated kinases. Anti-Cancer Drugs. 13, 859-868 (2002).

Ramana et al. Mitogenic responses of vascular smooth muscle cells to lipid peroxidation-derived aldehyde 4-hydroxytrans-2-nonenal (HNE): role of aldose reductase-catalyzed reduction of the HNE-glutathione conjugates in regulating cell growth. J Biol Chem. 281(26),17652-60 (2006).

Schneider et al. Tissue Distribution and Biotransformation of Zopolrestat, an Aldose Reductase Inhibitor, in Rats. Drug Metab Dispos. 26(11), 1149-59 (1998).

\* cited by examiner

*Primary Examiner* — Manjunath Rao
*Assistant Examiner* — Samuel Liu
(74) *Attorney, Agent, or Firm* — Norton Rose Fulbright US LLP

(57) ABSTRACT

Certain embodiments are directed to methods of treating a pathophysiological state or symptoms thereof resulting from aldose reductase-mediated signaling in a cytotoxic pathway using an aldose reductase specific inhibitor.

1 Claim, 10 Drawing Sheets

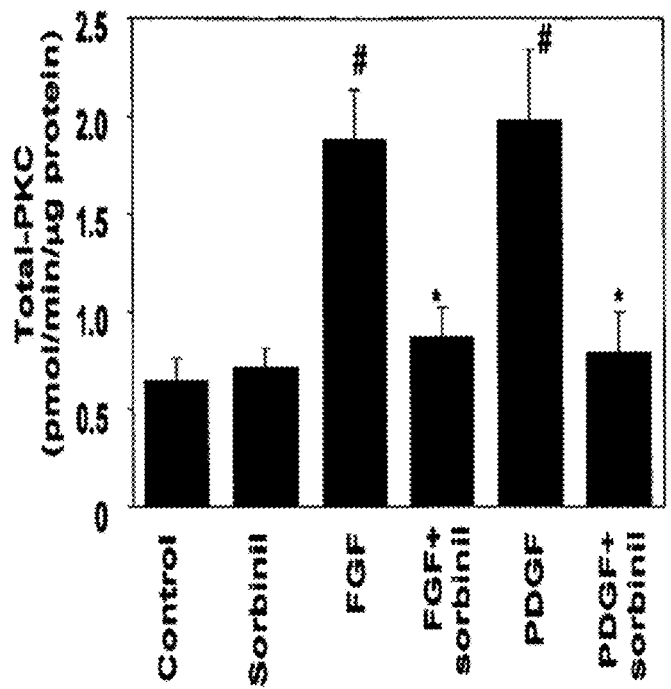
FIG. 3A
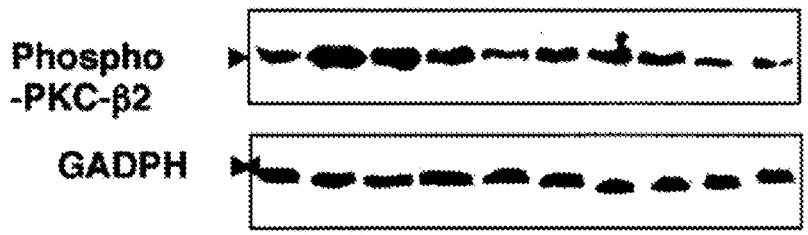
FIG. 3B
FIG. 3C
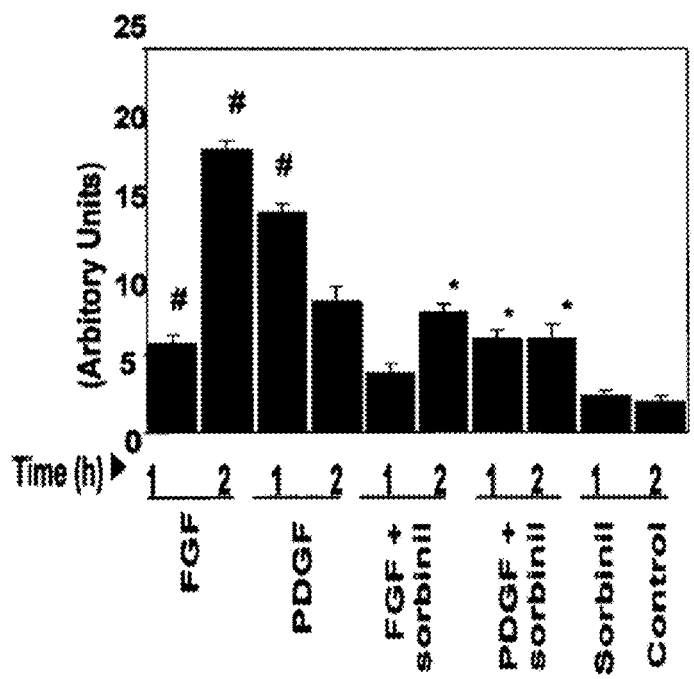
FIG. 3D

SEQUENCE LISTING

```
<160> NUMBER OF SEQ ID NOS: 7

<210> SEQ ID NO 1
<211> LENGTH: 21
<212> TYPE: DNA
<213> ORGANISM: artificial sequence
<220> FEATURE:
<223> OTHER INFORMATION: aldose reductase siRNA

<400> SEQUENCE: 1
aatcggtgtc tccaacttca a                                              21

<210> SEQ ID NO 2
<211> LENGTH: 21
<212> TYPE: DNA
<213> ORGANISM: artificial sequence
<220> FEATURE:
<223> OTHER INFORMATION: scrambled sequence of siRNA control

<400> SEQUENCE: 2
aaaatctccc taaatcatac a                                              21

<210> SEQ ID NO 3
<211> LENGTH: 10
<212> TYPE: DNA
<213> ORGANISM: artificial sequence
<220> FEATURE:
<223> OTHER INFORMATION: NF-kappaB binding consensus sequence

<400> SEQUENCE: 3
gggactttcc                                                           10

<210> SEQ ID NO 4
<211> LENGTH: 19
<212> TYPE: DNA
<213> ORGANISM: artificial sequence
<220> FEATURE:
<223> OTHER INFORMATION: Cox-2 sense primer

<400> SEQUENCE: 4
aaacccactc caaacacag                                                 19

<210> SEQ ID NO 5
<211> LENGTH: 20
<212> TYPE: DNA
<213> ORGANISM: artificial sequence
<220> FEATURE:
<223> OTHER INFORMATION: Cox-2 antisense primer

<400> SEQUENCE: 5
tcatcaggca caggaggaag                                                20

<210> SEQ ID NO 6
<211> LENGTH: 20
<212> TYPE: DNA
<213> ORGANISM: artificial sequence
<220> FEATURE:
<223> OTHER INFORMATION: beta-actin sense primer

<400> SEQUENCE: 6
tgagaccttc aacacccagg                                                20

<210> SEQ ID NO 7
<211> LENGTH: 24
<212> TYPE: DNA
<213> ORGANISM: artificial sequence
```

```
<220> FEATURE:
<223> OTHER INFORMATION: beta-actin antisense primer

<400> SEQUENCE: 7
ttcatgaggt agtctgtcag gtcc                                          24
```

COMPOSITIONS AND METHODS FOR TREATING COLON CANCER

STATEMENT REGARDING PRIORITY

This application claims priority to and is a continuation-in-part of U.S. application Ser. No. 12/586,050 (pending) filed Sep. 16, 2009, which is a continuation of U.S. application Ser. No. 11/478,069 (abandoned) filed Jun. 29, 2006 and is a continuation-in-part of U.S. application Ser. No. 11/282,801 (U.S. Pat. No. 7,702,430) filed Nov. 18, 2005, which claims benefit of provisional U.S. Ser. No. 60/629,448 filed Nov. 19, 2004. This application also claims priority to and is a continuation in part of U.S. application Ser. No. 11/210,283 (pending) filed Aug. 23, 2005, which claims priority to U.S. Provisional Application 60/603,725 filed on Aug. 23, 2004. The current application claims priority to all of the above referenced applications, all of which are hereby incorporated by reference in their entirety.

STATEMENT REGARDING FEDERALLY FUNDED RESEARCH

This invention was made with government support under DK36118, HL55477, EY01677, and HL59378 awarded by the National Institutes of Health. The government has certain rights in the invention.

REFERENCE TO SEQUENCE LISTING

A sequence listing required by 37 CFR 1.821-1.825 is being submitted electronically with this application. The sequence listing is incorporated herein by reference.

BACKGROUND

Aldose reductase (AR) is a monomeric $(\alpha/\beta)_8$-barrel (TIM barrel) protein belonging to the aldo-keto reductase (AKR) superfamily (Jez et al. (1997) *Biochem. J.* 326: 625-636; Rondeau et al. (1992) *Nature* 355:469-72; Wilson et al. (1992) *Science* 257:81-84). Aldose reductase is a broad-specificity oxidoreductase catalyzing the reduction of a structurally-diverse range of aldehydes, including medium to long chain aldehydes, glucose and other aldo-sugars, aldehyde metabolites of neurotransmitters, isocorticosteroid hormones, and a variety of xenobiotic aldehydes to their corresponding alcohols (Bhatnagar et al. (1992) *Biochem. Med. Metab. Biol.* 48:91-121). Reduction of glucose to sorbitol by aldose reductase constitutes the first and rate-limiting step of the polyol pathway that converts glucose to fructose via sorbitol dehydrogenase. Although this pathway usually represents a minor route of glucose metabolism, its activation during diabetes has been linked to the development of several clinically significant secondary complications such as nephropathy, neuropathy, retinopathy and cardiovascular related complications (Bhatnagar et al. (1992) *Biochem. Med. Metab. Biol.* 48:91-121; Nishikawa et al. (2000) *Kidney Int.* Suppl. 77:S26-30). Several drugs that inhibit aldose reductase have been shown to prevent hyperglycemia-induced changes in nerve, kidney, and lens of experimental animals, although clinical trials with Type I and Type II diabetics have not been uniformly positive (Bhatnagar et al. (1992) *Biochem. Med. Metab. Biol.* 48:91-121; Nishikawa et al. (2000) *Kidney Int.* Suppl. 77:S26-30; Parry (1999) *Am J Med* 107:27S-33S).

In addition to glucose, it has been shown that aldose reductase catalyzes the reduction of multiple biologically-active aldehydes generated by the peroxidation of membrane lipids and lipoproteins (Srivastava et al. (1995) *Biochem. Biophys. Res. Commun.* 217:741-746; Srivastava et al. (1998) *Biochem. J.* 329:469-475; Srivastava et al. (1999) *Biochemistry* 38:42-54) or during glucose (van der Jagt et al. (1992) *J. Biol. Chem.* 267:4364-4369) and amine (Kawamura et al. (1999) *Biochem Pharmacol* 58:517-24) metabolism. The aldehyde-detoxifying role of aldose reductase is supported by the observation that inhibition of the enzyme increases the accumulation of lipid peroxidation products (Rittner et al. (1999) *J Clin Invest* 103:1007-13; Shinmura et al. (2002) *Circ Res* 91:240-612) that cause cytotoxicity (Ruef et al. (2000) *Arterioscler Thromb Vase Biol* 20:1745-52; Ramana et al. (2002) *J Biol Chem* 277(35):32063-70). The most abundant and toxic lipid peroxidation product is 4-hydroxy-trans-2-nonenal (16) which is efficiently reduced by aldose reductase in vitro and in vivo.

SUMMARY

Certain embodiments are directed to methods of preventing a pathophysiological state or treating symptoms thereof resulting from aldose-reductase mediated signaling of a cytotoxic pathway in a subject. Embodiments are directed further still to a related methods of treating a pathophysiological state or symptoms thereof resulting from aldose reductase-mediated signaling in a cytotoxic pathway in a subject. The method comprises administering a pharmacologically effective amount of an inhibitor of aldose reductase to the subject thereby preventing aldose reductase mediated signaling.

Certain embodiments are directed to methods of treating or preventing cancer. The present invention is directed further still to another related method of treating cancer, such as colon cancer, in a subject. The method comprises administering a pharmacologically effective amount of an aldose reductase inhibitor to the subject to inhibit colon cancer cell proliferation thereby treating the cancer.

Certain embodiments are directed to methods of treating a subject having colon cancer comprising, administering a pharmacologically effective amount of a composition comprising an aldose reductase specific inhibitor to the subject having colon cancer. In certain aspects the aldose reductase specific inhibitor is selected from ponalrestat, tolrestat, epalrestat, zenarestat, sorbinil, fidarestat, minalrestat, or zopolrestat. In a further aspect the aldose reductase specific inhibitor is fidarestat.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof. As used herein, the term "subject" refers to any target of the treatment.

The following abbreviations are used herein: AR: aldose reductase or human aldose reductase, ARL2, E.C. 1.1.1.21; sAR: *Sus scrofa* (Pig) aldose reductase, AR, E.C. 1.1.1.21; ARI: aldose reductase inhibitor; NADPH: dihydronicotinamide-adenine-dinucleotide phosphate; NADP: nicotinamide-adenine-dinucleotide phosphate; DCEG: S-(1,2-dicarboxyethyl) glutathione, γ-glutamyi-S(1,2-dicarboxyethyl) cysteinylglycine; ROS: reactive oxygen species; CNS: Crystallography and NMR Software; GS or GSH: glutathione; γ-glutamylcysteinylglycine; GS-HNE: glutathionyl-4-hydroxynonenal; GS-DHN: glutathionyl-1,4-dihydroxynonene; PGE2: prostaglandin E2; MTT: [3-(4,5-dimethylthiazol-2-yl)-5-(3-carboxymethoxyphenyl)-2-(4-sulfophenyl)-2H-tetrazolium salt]; bFGF: basic fibroblast growth factor; Cox: cyclooxygenase; DHN: 1,4-dihydroxynonene; HNE: 4-hydroxy-trans-2-nonenal; NF-kB: nuclear factor kappa binding protein; PKC: Protein kinase C; PDGF: Platelet derived growth factor; SEAP: Secretory alkaline phosphatase.

Other and further aspects, features, and advantages of the present invention will be apparent from the following description of the embodiments of the invention given for the purpose of disclosure.

DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate embodiments of the invention and therefore are not to be considered limiting in their scope.

FIG. 1G is a densitometric analysis of FIG. 1D. Bars represent mean±S.E. (n=4); # $p<0.001$ compared with treatment without the inhibitor or scrambled oligo transfected cells and * $p<0.01$; **, $p<0.001$ compared with growth factor treated cells.

FIGS. 2A-2B measure Cox-2 and β-actin expression, respectively. FIG. 2C is a densitometric analysis of FIG. 2A. FIG. 2D shows NF-kB-dependent reporter SEAP activity. The Inset in FIG. 2D shows the chemiluminescence of SEAP.

FIGS. 3A-3F illustrate that the inhibition of AR abrogates growth factor-induced PKC activation and growth in colon cancer cells. Quiescent Caco-2 cells were preincubated with sorbinil for 24 h followed by stimulation with bFGF or PDGF for 3 h. FIG. 3A shows membrane-bound PKC activity. Western blot analysis using antibodies against phospho-PKC-β2 (FIG. 3B) and GAPDH (FIG. 3C) are depicted. FIG. 3D is a densitometric analysis of FIG. 3B. Growth-arrested Caco-2 cells were preincubated with or without sorbinil or tolrestat (FIG. 3E) or were transfected with AR antisense oligo followed by stimulation with bFGF or PDGF for 24 h and cell viability was measured by MTT assay (FIG. 3F). Bars represent mean±S.E. (n=4); # $p<0.01$ as compared to control cells. * $p<0.01$ compared to cells treated with growth factors.

FIG. 6A illustrates PGE2 production. Western blots were developed using antibodies against Cox-2 (FIG. 6B) and GAPDH (FIG. 6C). FIG. 6D is a densitometric analysis of FIG. 6B. Bars represent mean±S.E. (n=4); # $p<0.001$ Vs. control cells and *$p<0.01$ Vs. cells treated with aldehydes.

DESCRIPTION

Figure 1A:
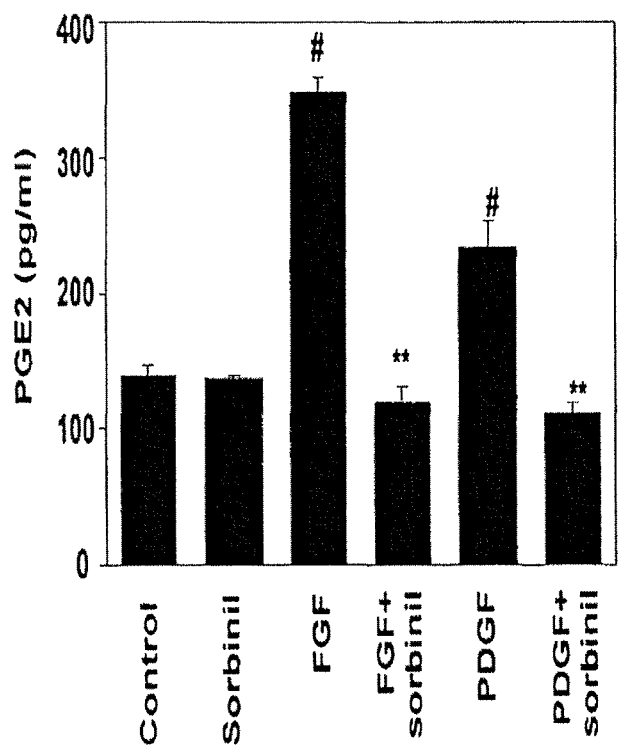
FIGS. 1A-1G illustrate that Inhibition or ablation of AR prevents growth factor-induced PGE2 production and Cox-2 expression in colon cancer cells. Growth-arrested Caco-2 cells were pre-incubated with sorbinil or carrier for 24 h (FIG. 1A) and with AR antisense or scrambled oligos (FIG. 1B). The inset in FIG. 1B represents Western blot analysis for AR protein in untransfected (c), scrambled (s) and AR antisense (a) oligo transfected cell extracts. The AR inhibited and ablated cells were stimulated with bFGF or PDGF, as in FIG. 2A, except that Cox activity was measured by a Cox activity assay kit (FIG. 1C). Western blots were developed using antibodies against Cox-2 (FIG. 1D), Cox-1 (FIG. 1E) and GAPDH (FIG. 1F).

Certain embodiments are directed to methods of preventing a pathophysiological state or treating symptoms thereof resulting from aldose-reductase mediated signaling of a cytotoxic pathway in a subject, comprising administering a pharmacologically effective amount of the inhibitor described herein to the subject; and inhibiting the reduction of a glutathione-aldehyde substrate via aldose reductase, thereby preventing the cytotoxic signaling in the subject. An example of a pathophysiological state is colon cancer or one comprising inflammation. An example of a cytotoxic pathway is PLC/PKC/NFKB or other NF-KB dependent inflammatory processes, for example, due to a bacterial infection.

In another related embodiment there is provided a method of treating a pathophysiological state or symptoms thereof resulting from aldose reductase-mediated signaling in a cytotoxic pathway in a subject, comprising administering a pharmacologically effective amount of an inhibitor of aldose reductase to the subject thereby preventing aldose reductase mediated signaling.

In one aspect the inhibitor may be a small interfering RNA (siRNA). An example of an siRNA has the sequence of SEQ ID NO: 1. Alternatively, the siRNA may comprise a vector effective to transfect a cell characteristic of the pathophysiological state. A person having ordinary skill in this art would readily recognize that any method to reduce aldose reductase, e.g., antisense molecules or aldose reductase inhibitors, may be utilized. A representative example of such a cell is a colon cancer cell, although any cancer cell may be targeted in this manner.

In certain embodiments the pathophysiological state may be a cancer. A representative example of a cancer is colon cancer. Furthermore, the cytotoxic pathway may be a PLC/PKC/NF-KB pathway. Inhibition of this pathway may inhibit signaling by one or more of NF-KB, prostaglandin 2 (PGE2) or cyclooxygenase (Cox-2).

In yet another related embodiment there is provided a method of treating colon cancer in a subject, comprising administering a pharmacologically effective amount of an aldose reductase small interfering RNA (siRNA) to the subject to inhibit colon cancer cell proliferation thereby treating the colon cancer. The siRNA or vector comprising the same are as described supra.

Provided herein is a crystallized ternary complex of human aldose reductase bound to NADPH and γ-glutamyi-S-(1,2-dicarboxyethyl)cysteineinylglycine, a competitive inhibitor of AR-catalyzed reaction of glutathionyl-propanal (19). The ternary structure confirms the presence of two active sites within AR:NADPH. The crystal structure was determined to 1.9 Å and revealed novel interactions between the glutathione backbone and active site residues.

Certain embodiments are directed to methods of inhibiting expression of aldose reductase at the RNA translational level. It is contemplated that administration of aldose reductase small interfering RNAs (siRNA) is useful in the treatment of a pathophysiological state, such as a cancer. It is specifically contemplated that inhibiting expression of aldose reductase will be useful in treating any type of cancer. A representative cancer is colon cancer. The siRNAs may be useful in the treatment of or alleviation of other pathophysiological conditions or symptoms resulting from aldose reductase-mediated signaling of a cytotoxic pathway. For example, conditions exhibiting or characterized by inflammation, e.g., lipopolysaccharide-induced inflammation, may benefit from such treatment or therapy.

The design methodology for siRNAs is known in the art and/or they may be obtained commercially. For example, without being limiting, an siRNA effective as a therapeutic may have the sequence of SEQ ID NO: 1. siRNAs may be administered to a subject as the naked oligomer or as comprising a suitable transfection vector or with a carrier molecule or moiety as are known and standard in the art.

It is standard in the art to formulate a therapeutic compound with a pharmaceutically acceptable carrier as a pharmaceutical composition. It is also standard in the art to determine dose, dosage and routes of administration of the therapeutic or pharmaceutical compounds. Such determination is routinely made by one of skill in the art based on the individual and the particular pathophysiological state or symptoms exhibited by the patient and the patient's history.

I. Aldose Reductase Inhibitors

The inhibitors of aldose reductase can be any compound that inhibits the enzyme aldose reductase. It is contemplated that the aldose reductase inhibitors provided herein may be used as a therapeutic to treat or modulate or otherwise alter a pathophysiological state or event or symptoms thereof mediated by reduction products of aldose reductase as part of the pathology. For example, and without being limiting, a specific inhibitor could prevent glutathione binding without affecting the carbonyl reduction necessary to detoxify lipid aldehydes. Such inhibition could regulate TNF-α, growth factor, lipopolysaccharide and hyperglycemia-induced cytotoxicity mediated by reactive oxygen species in for example, the PLC/PKC/NF-kB pathway. It is further contemplated that such an inhibitor may limit access of other bulky molecules, such as glucose, to the AR active site thereby reducing other adverse effects of hyperglycemia as mediated by AR's role in the osmotic stress pathway.

It is contemplated that an aldose reductase inhibitor may specifically bind or recognize a particular region of AR, including 300, 350, 375, 385 or greater contiguous amino acids of aldose reductase or any range of numbers of contiguous amino acids derivable therein. The aldose reductase inhibitor compounds of this invention are readily available or can be easily synthesized by those skilled in the art using conventional methods of organic synthesis, particularly in view of the pertinent patent specifications. Many of these are well known to those of skill in the art, and a number of pharmaceutical grade AR inhibitors are commercially available, such as Tolrestat, N-[[6-methoxy-5-(trifluoromethyl)-1-naphthalenyl]thioxomethyl]-N-methylglycine, [Wyeth-Ayerst, Princeton, N.J.; other designations are Tolrestatin, CAS Registry Number 82964-04-3, Drug Code AY-27,773, and brand names ALREDASE (Am. Home) and LORESTAT (Recordati)]; Ponalrestat, 3-(4-bromo-2-fluorobenzyl)-4-oxo-3H-phthalazin-1-ylacetic acid [ICI, Macclesfield, U.K.; other designations are CAS Registry Number 72702-95-5, ICI-128,436, and STATIL (ICI)]; Sorbinil, (S)-6-fluoro-2,3-dihydrospiro[4H-1-benzopyran-4,4'-imidazolidine]-2',5'-dione (Pfizer, Groton, Conn.; CAS Registry Number 68367-52-2, Drug Code CP-45,634); EPALRESTAT (ONO, Japan); METHOSORBINIL (Eisal); ALCONIL (Alcon); AL-1576 (Alcon); CT-112 (Takeda); AND-138 (Kyorin).

A variety of aldose reductase inhibitors are specifically described and referenced below, however, other aldose reductase inhibitors will be known to those skilled in the art. Also, common chemical USAN names or other designations are in parentheses where applicable, together with reference to appropriate patent literature disclosing the compound. Accordingly, examples of aldose reductase inhibitors useful in the compositions, methods and kits of this invention include, but are not limited to: 3-(4-bromo-2-fluorobenzyl)-3,4-dihydro-4-oxo-1-phthalazineacetic acid (ponalrestat, U.S. Pat. No. 4,251,528); N[[(5-trifluoromethyl)-6-methoxy-1-naphthalenyl]thioxomethyl]-N-methylglycine (tolrestat, U.S. Pat. No. 4,600,724); 5-[(Z,E)-β-methylcinnamylidene]-4-oxo-2-thioxo-3-thiazolideneacetic acid (epalrestat, U.S. Pat. Nos. 4,464,382, 4,791,126, and 4,831,045); 3-(4-bromo-2-fluorobenzyl)-7-chloro-3,4-dihydro-2,4-dioxo-1(2H)-quinazolineacetic acid (zenarestat, U.S. Pat. Nos. 4,734,419, and 4,883,800); 2R,4R-6,7-dichloro-4-hydroxy-2-methyl-chroman-4-acetic acid (U.S. Pat. No. 4,883,410); 2R,4R-6,7-dichloro-6-fluoro-4-hydroxy-2-methylchroman-4-acetic acid (U.S. Pat. No. 4,883,410); 3,4-dihydro-2,8-diisopropyl-3-oxo-2H-1,4-benzoxazine-4-acetic acid (U.S. Pat. No. 4,771,050); 3,4-dihydro-3-oxo-4-[(4,5,7-trifluoro-2-benzothiazolyl)methyl]-2H-1,4-benzothiazine-2-acetic acid (SPR-210, U.S. Pat. No. 5,252,572); N-[3,5-dimethyl-4-[(nitromethyl)sulfonyl]phenyl]-2-methyl-benzeneacetamide (ZD5522, U.S. Pat. Nos. 5,270,342 and 5,430,060); (S)-6-fluorospiro[chroman-4,4'-imidazolidine]-2,5'-dione (sorbinil, U.S. Pat. No. 4,130,714); d-2-methyl-6-fluoro-spiro(chroman-4',4'-imidazolidine)-2',5'-dione (U.S. Pat. No. 4,540,704); 2-fluoro-spiro(9H-fluorene-9,4'-imidazolidine)-2',5'-dione (U.S. Pat. No. 4,438,272); 2,7-di-fluoro-spiro(9H-fluorene-9,4'-imidazolidine)-2',5'-dione (U.S. Pat. No. 4,436,745, U.S. Pat. No. 4,438,272); 2,7-di-fluoro-5-methoxy-spiro(9H-fluorene-9,4'-imidazolidine)-2',5'-dione (U.S. Pat. No. 4,436,745, U.S. Pat. No. 4,438,272); 7-fluoro-spiro(5H- indenol[1,2-b]pyridine-5,3'-pyrrolidine)-2,5'-dione (U.S. Pat. Nos. 4,436,745, 4,438,272); d-cis-6'-chloro-2',3'-dihydro-2'-methyl-spiro-(imidazolidine-4,4'-4'H-pyrano(2,3-b)pyridine)-2,5-dione (U.S. Pat. No. 4,980,357); spiro[imidazolidine-4,5'(6H)-quinoline]-2,5-dione-3'-chloro-7,'8'-dihydro-7'-methyl-(5'-cis) (U.S. Pat. No. 5,066,659); (2S,4S)-6-fluoro-2',5'-dioxospiro(chroman-4,4'-imidazolidine)-2-carboxamide (fidarestat, U.S. Pat. No. 5,447,946); and 2-[(4-bromo-2-fluorophenyl)methyl]-6-fluorospiro[isoquinoline-4(1H),3'-pyrrolidine]-1,2',3,5'(2H)-tetrone (minalrestat, U.S. Pat. No. 5,037,831). Other compounds include those described in U.S. Pat. Nos. 6,720,348, 6,380,200, and 5,990,111, which are hereby incorporated by reference. Moreover, in other embodiments it is specifically contemplated that any of these may be excluded as part of the invention.

It is standard in the art to formulate a therapeutic compound with a pharmaceutically acceptable carrier as a pharmaceutical composition. It is also standard in the art to determine dose, dosage and routes of administration of the therapeutic or pharmaceutical compounds. Such determination is routinely made by one of skill in the art based on the individual and the particular pathophysiological state or symptoms exhibited by the patient and the patients history.

II. Aldose Reductase Structure

The ternary structure demonstrates that DCEG binding induces a significant conformational reorganization of the active site. The carboxylate moiety of DCEG binds in the aldose reductase active site, while the GS C-terminus binds in the aldose reductase loop C. The binding of glutathione to aldose reductase significantly reorients loops A and B of the protein thereby providing an induced-fit mechanism that enables the active site to bind substrates of different sizes. This induced-fit rearrangement and the multiplicity of specific interactions at the aldose reductase active site with glutathione are indicative of a highly selective glutathione-binding domain.

Thus, the ternary structure is used in methods of developing therapeutic inhibitors that selectively prevent binding of glutathione-conjugated substrates. These structure-based inhibitors are designed using rational drug design in conjunction with computer modeling of the coordinates of the ternary crystalline structure.

The AR:NADPH:DCEG ternary complex structure was refined to 1.94 Å resolution with a final R-factor of 21.6%. This structure showed well-defined electron density for the DCEG substrate at the "top" of aldose reductase active site pocket. The DCEG was bound between two opposing surfaces of the active site pocket, but did not completely fill the active site cleft. The DCEG substrate made ~80 contacts, defined as inter-residue distances ≤4 Å, with residues in the active site cleft. The majority of these intermolecular contacts were hydrophobic. The NADPH binding site was located at the base of the aldose reductase hydrophobic active site pocket and the NADPH cofactor was bound to the ternary complex in an orientation identical to that observed in previously reported crystal structures (Wilson et al. (1992) *Science* 257:81-84; Calderone et al. (2000) *Acta Crystallogr D Biol Crystallogr* 56:536-40; Urzhumtsev et al. (1997) *Structure* 5:601-12).

The active site of aldose reductase sat at the base of a deep cleft or binding pocket. The sides of the active site pocket were formed by three flexible loops A, B, and C that sat on top of the aldose reductase $(\alpha\beta)_8$ barrel. The active site comprises residues Tyr-48, His-110, and Trp-111. DCEG was bound in the active site almost filling the active site pocket. Trp-219 forms one side of the narrow pocket holding the inhibitor DCEG. The other residues lining this pocket included Trp-20, Trp-79, Trp-111, Phe-122, NADPH, Val-47, Cys-298, Ala-299, Leu-300, and Leu-301.

The C-terminal glycine moiety of DCEG was extensively hydrogen bonded to the backbone atoms of residues 300-302 in the flexible human aldose reductase C-terminal loop (loop-C). In addition, the ligand made several van der Waals contacts with aldose reductase. Several bound water molecules mediated the interaction between the DCEG glycine moiety and aldose reductase. The amides of Ala-299 and Leu-300 were bound indirectly to DCEG through a water molecule. The terminal carboxylate group of the DCEG interacted with the backbone of Leu-301 and Ser-302 and indirectly with Leu-301 through a network of waters. These residues were in human aldose reductase loop C, which has been shown to be important for enzymatic activity. Mutations within this loop result in drastically lowered human aldose reductase activity (Bohren et al. (1992) *J Biol Chem* 267:20965-70).

The dicarboxyethyl group of DCEG was anchored in the conserved anion-binding site between the nicotinamide ring of the NADPH cofactor and aldose reductase residues Tyr-48, His-110, and Trp-111 similar to other known aldose reductase inhibitors (Calderone et al. (2000) *Acta Crystallogr D Bioi Crystallogr* 56:536-40; Urzhumtsev et al. (1997) *Structure* 5:601-12). The terminal carboxylates of the dicarboxyethyl conjugate's longer arm, Oi2 and Oj2, were hydrogen bonded to active site residues His-110, Tyr-48, and Trp-111. The γ-glutamate of DCEG was observed to interact with the AR enzyme only through van der Waals contacts with Phe-122 that formed one side of the hydrophobic active site pocket. The lack of hydrogen bonds or extensive contacts permitted the γ-glutamate moiety significant conformational freedom.

The higher temperature factors for these atoms reflected the relative disorder in the N-terminal end of DCEG. The hydrophobic walls of the upper portion of the aldose reductase active site pocket were formed in large part by Trp-219 and Phe-122, similar to the structures observed in other AR:inhibitor complexes (Calderone et al. (2000) *Acta Crystallogr D Bioi Crystallogr* 56:536-40; Urzhumtsev et al. (1997) *Structure* 5:601-12). These two aromatic residues tightly constrained the position of the cysteine moiety in DCEG. The Phe-122 and Trp-219 side chains could move slightly to accommodate differently sized inhibitors. The extensive van der Waals contacts with Trp-20 observed in the aromatic inhibitors tolrestat, zopolrestat, and sorbinil were completely absent in DCEG. The Trp-20 and Trp-79 residues, although still defining the active site pocket, did not interact with DCEG directly. They did, however, limit the conformational space available to the DCEG molecule.

The structure of the human aldose reductase enzyme within the ternary complex showed significant conformational differences relative to the AR:NADPH binary complex (Wilson et al. (1992) *Science* 257:81-84). The backbone atoms of Pro-123 to Val-131 in loop A and Pro-218 to Pro-225 in loop B, which flank the active site pocket, were reoriented >5 Å upon DCEG binding relative to the binary structure. The AR:NADPH:DCEG ternary complex more closely resembled the AR:NADP:zopolrestat (Wilson et al. (1993) *PNAS* 90:9847-51) and AR:NADP:Idd384 (Calderone et al. (2000) *Acta Crystallogr D Bioi Crystallogr* 56:536-40) ternary complexes than the AR:NADPH binary complex. In the ternary complexes the largest relative atomic movements, with rmsd >1 Å, occurred in the region of Ser-127, Pro-222, and Leu-300.

The conformation of loop B, residues Pro-218 to Pro-225, was very similar in all of the AR structures, with just the backbone conformation of residues Pro-222 and Asp-224 flipping in the holoenzyme. Loop A of the holoenzyme structure (Wilson et al. (1992) *Science* 257:81-84) displayed a completely different conformation for this entire loop region relative to the current complex. Loop C was observed in two different conformations, which depended on the size and shape of the inhibitor bound in the solved AR structures. The conformation of loop C in AR:NADPH:DCEG had the greatest similarity to the human aldose reductase structures found in the AR:NADPH holoenzyme (Wilson et al. (1992) *Science* 257:81-84) and AR:NADPH:Idd384 ternary complex (Calderone et al. (2000) *Acta Crystallogr D Bioi Crystallogr* 56:536-40). Additionally, loop C in the current structure had large positional differences with the conformation observed in the zoplorestat and tolrestat ternary complexes (Urzhumtsev et a. (1997) *Structure* 5:601-12). This indicated that loop C was dynamic and could move to accommodate larger molecules such as zopolrestat and tolrestat. The smaller sorbinil inhibitor did not change this loop's conformation significantly (Urzhumtsev et a. (1997) *Structure* 5:601-12).

III. Pharmaceutical Compositions and Routes of Administration

Pharmaceutical compositions of the present invention may comprise an effective amount of one or more AR inhibitors dissolved or dispersed in a pharmaceutically acceptable carrier to a subject. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one AR inhibitor or additional active ingredient will be known to those of skill in the art in light of the present disclosure, and as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for, example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated. An AR inhibitor can be administered in the form of a pharmaceutically acceptable salt or with a pharmaceutically acceptable salt.

The expression "pharmaceutically acceptable salts" includes both pharmaceutically acceptable acid addition salts and pharmaceutically acceptable cationic salts, where appropriate. The expression "pharmaceutically-acceptable cationic salts" is intended to define but is not limited to such salts as the alkali metal salts, (e.g., sodium and potassium), alkaline earth metal salts (e.g., calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol) and procaine. The expression "pharmaceutically-acceptable acid addition salts" is intended to define but is not limited to such salts as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts.

Pharmaceutically acceptable salts of the aldose reductase inhibitors of this invention may be readily prepared by reacting the free acid form of the aldose reductase inhibitor with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine and tromethamine. The salt is isolated by concentration to dryness or by addition of a non-solvent. In many cases, salts are preferably prepared by mixing a solution of the acid with a solution of a different salt of the cation (sodium or potassium ethylhexanoate, magnesium oleate), and employing a solvent (e.g., ethyl acetate) from which the desired cationic salt precipitates, or can be otherwise isolated by concentration and/or addition of a non-solvent.

The acid addition salts of the aldose reductase inhibitors of this invention may be readily prepared by reacting the free base form of said aldose reductase inhibitor with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However when such salts as the sulfate, the hemisuccinate, the hydrogen phosphate, or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

The pharmaceutically acceptable acid addition and cationic salts of antibiotics used in the combination of this invention may be prepared in a manner analogous to that described for the preparation of the pharmaceutically acceptable acid addition and cationic salts of the aldose reductase inhibitors.

In addition, the aldose reductase inhibitors that may be used in accordance with this invention, prodrugs thereof and pharmaceutically acceptable salts thereof or of said prodrugs, may occur as hydrates or solvates. These hydrates and solvates are also within the scope of the invention.

A pharmaceutical composition of the present invention may comprise different types of carriers depending on whether it is to be administered in solid, liquid or aerosol form, and whether it needs to be sterile for such routes of administration as injection. A pharmaceutical composition of the present invention can be administered intravenously, intradermally, intraarterially, intraperitoneally, intraarticularly, intrapleurally, intranasally, topically, intramuscularly, intraperitoneally, subcutaneously, subconjunctival, intravesicularlly, mucosally, intrapericardially, intraumbilically, orally, topically, locally, inhalation (e.g., aerosol inhalation), injection, infusion, continuous infusion, via a catheter, via a lavage, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to a subject can be determined by physical and physiological factors such as body weight, severity of condition, the type of disease being treated, previous or concurrent therapeutic interventions, idiopathy of the patient and on the route of administration. The number of doses and the period of time over which the dose may be given may vary. The practitioner responsible for administration will, in any event, determine the concentration of active ingredient(s) in a composition and appropriate dose(s), as well as the length of time for administration for the individual subject. An amount of an aldose reductase inhibitor that is effective for inhibiting aldose reductase activity is used. Typically, an effective dosage for the inhibitors is in the range of about 0.01 mg/kg/day to 100 mg/kg/day in single or divided doses, preferably 0.1 mg/kg/day to 20 mg/kg/day in single or divided doses. Doses of about, at least about, or at most about 0.01, 0.05, 0.1, 0.15, 0.20, 0.25, 0.30, 0.35, 0.40, 0.45, 0.50, 0.55, 0.60, 0.65, 0.70, 0.75, 0.80, 0.85, 0.90. 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg/day, or any range derivable therein.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

An AR inhibitor(s) of the present invention may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In certain aspects of the invention, the AR inhibitors are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

In order to increase the effectiveness of treatments with the compositions of the present invention, such as an AR inhibitor, it may be desirable to combine it with other therapeutic agents. This process may involve contacting the cell(s) with an AR inhibitor and a therapeutic agent at the same time or within a period of time wherein separate administration of the modulator and an agent to a cell, tissue or organism produces a desired therapeutic benefit. The terms "contacted" and "exposed," when applied to a cell, tissue or organism, are used herein to describe the process by which a AR inhibitor and/or therapeutic agent are delivered to a target cell, tissue or organism or are placed in direct juxtaposition with the target cell, tissue or organism. The cell, tissue or organism may be contacted (e.g., by administration) with a single composition or pharmacological formulation that includes both a AR inhibitor and one or more agents, or by contacting the cell with two or more distinct compositions or formulations, wherein one composition includes an AR inhibitor and the other includes one or more agents.

The AR inhibitor may precede, be concurrent with and/or follow the other agent(s) by intervals ranging from minutes to weeks. In embodiments where the AR inhibitor and other agent(s) are applied separately to a cell, tissue or organism, one would generally ensure that a significant period of time did not expire between the time of each delivery, such that the inhibitor and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the modulator. In other aspects, one or more agents may be administered within of from substantially simultaneously, about 1 minute, about 5 minutes, about 10 minutes, about 20 minutes about 30 minutes, about 45 minutes, about 60 minutes, about 2 hours, or more hours, or about 1 day or more days, or about 4 weeks or more weeks, or about 3 months or more months, or about one or more years, and any range derivable therein, prior to and/or after administering the AR inhibitor.

In such combinations, AR inhibitors and other active agents may be administered together or separately. In addition, the administration of one agent may be prior to, concurrent to, or subsequent to the administration of other agent(s).

IV. Examples

The following examples as well as the figures are included to demonstrate embodiments of the invention. It should be appreciated by those of skill in the art that the techniques disclosed in the examples or figures represent techniques discovered by the inventors to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Aldose Reductase Inhibition

Materials and Methods

Materials.

McCoy's 5A medium, Dulbecco's modified Eagle's medium (DMEM), phosphate-buffered saline (PBS), penicillin/streptomycin solution, trypsin, and fetal bovine serum (FBS) were purchased from Invitrogen. Antibodies against Cox-1, Cox-2 and phosphor-PKC-$\beta$2 were obtained from Santa Cruz Biotechnology, Inc. (Santa Cruz, Calif.). Sorbinil and tolrestat were gifts from Pfizer and American Home Products, respectively. Mouse anti-rabbit glyceraldehyde-3-phosphate dehydrogenase antibodies were obtained from Research Diagnostics Inc.

Cyclooxygenase (Cox) activity assay and prostaglandin E2 (PGE2) assay kits were obtained from Cayman Chemical Company (Ann Arbor, Mich.). Platelet-derived growth factor (PDGF), basic fibroblast growth factor (bFGF), 3-(4,5-dimethylthiazol-2-yl)-2,5-diphenyltetrazolium bromide (MTT), and other reagents used in the Electrophoretic Mobility Shift Assay (EMSA) and Western blot analysis were obtained from Sigma. AR-siRNA (5'AATCGGTGTCTCCAACTTCAA-3'; SEQ ID NO:1) or scrambled siRNA (control) (5'-AAAATCTCCCTAAATCATACA-3'; SEQ ID NO:2) were synthesized by Dharmacon Research. All other reagents used were of analytical grade.

Cell Culture.

Human colon cancer cell lines, HCT-116 and Caco-2 were obtained from American type culture collection (ATCC). HCT-116 cells were maintained and grown in McCoy's 5A medium supplemented with 10% FBS and 1% penicillin/streptomycin and Caco-2 cells were grown in DMEM with 10% FBS and 1% penicillin/streptomycin at 37° C. in a humidified atmosphere of 5% $CO_2$. Human colon adenocarcinoma (SW480) cells were purchased from ATCC and cultured at 37° C. in a humidified atmosphere of 5% $CO_2$ in RPMI-1640 medium supplemented with 10% (v/v) heat-inactivated FBS, 1% (v/v) P/S solution, 2 mM L-glutamine, 10 mM HEPES, 1 mM sodium pyruvate, 4.5 g/L glucose, and 1.5 g/L sodium bicarbonate.

Measurement of Cytotoxicity.

Caco-2 cells were grown to confluency in DMEM medium, harvested by trypsinization and plated ~2500 cells/well in a 96-well plate. Subconfluent cells were growth-arrested in 0.1% FBS. After 24 h, 10 ng/ml of bFGF or PDGF without or with AR inhibitors sorbinil or tolrestat were added to the media and the cells were incubated for another 24 h. Cells incubated with the AR inhibitors alone served as control. Cell viability was determined by cell count and MTT-assay as described earlier (Ramana et al. (2002) *J Biol Chem* 277(35): 32063-70; Ramana et al. (2004) *FEBS Lett* 570(1-3):189-194; Ramana et al. (2003) *FASEB J.* 17(2):315-317).

Determination of PKC Activity.

PKC activity was measured using the Promega-Sigma TECT PKC assay system as described earlier (Ramana et al. (2002) *J Biol Chem* 277(35):32063-70). Briefly, aliquots of the reaction mixture (25 mM Tris-HCl pH 7.5, 1.6 mg/mL phosphatidylserine, 0.16 mg/mL diacylglycerol, and 50 mM $MgCl_2$) were mixed with [$^{32}$P] ATP (3,000 Ci/mmol, 10 µCi/µL) and incubated at 30° C. for 10 min. To stop the reaction, 7.5 M guanidine hydrochloride were added and the phosphorylated peptide was separated on binding paper. The extent of phosphorylation was detected by measuring radioactivity retained on the paper.

PGE2 Assay.

Caco-2 cells were plated in 6 well plates at a density of $2\times10^5$ cells/well. After 24 hours, the medium was replaced with fresh medium containing 0.1% serum with or without, sorbinil (20 µM) followed by treatment with either 10 ng/ml bFGF or PDGF, for another 24 h. The medium was collected from each well and analyzed for PGE2 by using an Enzyme Immuno Assay kit according to the manufacturer's instructions (Cayman Chemical Co., Inc.).

Briefly, 50 µl of diluted standard/sample were pipetted into a precoated goat polyclonal anti-mouse IgG 96-well plate. Aliquots (50 µl) of a PGE2 monoclonal antibody and PGE2 acetylcholine esterase (AChE) conjugate, (PGE2 tracer) were added to each well and allowed to incubate at 4° C. for 24 h. After incubation, the wells were washed five times with wash buffer containing 0.05% Tween-20, followed by the addition of 200 µl of Ellman's reagent containing acetylthiocholine and 5,5'-dithio-bis-(2-nitrobenzoic acid). Samples were read after 60 min at 412 nm with an ELISA reader. In this procedure the intensity of yellow color, is proportional to the amount of PGE2 tracer bound to the well and is inversely proportional to the amount of free PGE2 present in the well during incubation.

Cyclooxygenase Activity Assay.

For determination of Cox activity growth-arrested Caco-2 cells were treated with either 10 ng/ml bFGF or PDGF in the absence and presence of sorbinil (20 µM) for 24 h. The cells were harvested and homogenized in cold (4° C.) buffer containing 0.1M Tris-HCl, pH 7.8 and 1 mM EDTA and the activity was measured in 96 well plate according to the manufacturer's (Cayman Chemical Co., Inc.) instructions. Briefly, 10 µl of standard/sample were incubated in the presence of arachidonic acid and substrate, N,N,N,N-tetra methyl-p-phenylenediamine (TMPD) in a total reaction volume of 210 µl. The Cox peroxidase activity was measured calorimetrically by monitoring appearance of oxidized TMPD at 590 nm by using ELISA reader.

NF-KB-Dependent Reporter Secretory Alkaline Phosphatase CSEAP> Expression Assay.

Caco-2 cells ($1.5\times10^5$ cells/well) were plated in six-well plates and after attachment overnight, were serum-starved in optiMEM medium for 24 h with or without aldose reductase inhibitor, sorbinil (20 µM) and were transiently transfected with pNF-KB-SEAP construct or control plasmid pTAL-SEAP DNA (Clontech, USA) using the lipofectamine plus reagent. After 6 h of transfection, cells were treated either with 10 ng/ml bFGF or PDGF for 48 h in DMEM medium containing 0.1% FBS. The cell culture medium was then harvested and analyzed for SEAP activity, essentially as described by the manufacturer (Clontech Laboratories, Palo Alto, Calif.), using a 96-well chemiluminescence plate reader and Kodak Image Station 2000R.

Determination of NF-KB Activation.

The cytosolic as well as nuclear extracts were prepared as described earlier (Ramana et al. (2002) *J Biol Chem* 277(35): 32063-70) and the NF-kB activity was determined by using the colorimetric non-radioactive NF-kB p65 Transcription Factor Assay kit (Chemicon Intl.) as per the supplier's instructions. Briefly, a double stranded biotinylated oligonucleotide containing the consensus sequence for NF-kB binding (5'GGGACTTTCC-3'; SEQ ID NO:3) was mixed with nuclear extract and assay buffer. After incubation, the mixture (probe+extract+buffer) was transferred to the streptavidin-coated ELISA kit and read at 450 nm using an ELISA plate reader. For each experiment, triplicate samples were measured for statistical significance.

RT-PCR.

Total RNA was isolated from Caco-2 cells by using RNaeasy™ micro isolation kit (Qiagen). Total RNA (1.5 µg) sample was reverse transcribed with Omniscript™ and Sensiscript™ reverse transcriptase one-Step RT PCR system with HotStarTaq™ DNA polymerase (Qiagen) at 55° C. for 30 min followed by PCR amplification. The oligonucleotide primer sequences were as follows: 5'-AAACCCACTC-CAAACACAG-3' (sense; SEQ ID NO:4) and 5'-TCATCAG-GCACAGGAGGAAG-3' (antisense; SEQ ID NO:5) for Cox-2, and 5'-TGAGACCTICAACACCCCAG-3' (SEQ ID NO:6) and 5'-TTCATGAGGTAGTCTGTCAGGTCC-3' (SEQ ID NO:7) for β-actin. PCR reaction was carried out in a Gene-Amp™ 2700 thermocycler (Applied Biosystems, Foster City, Calif.) under the following conditions: initial denaturation at 95° C. for 15 min; 35 cycles of 94° C. 30 s, 62° C. 30 s, 72° C. 1 min, and then 72° C. 5 min for final extension (Smith et al. (2000) *Eur. J. Cancer* 36(5):664-674). PCR products were electrophoresed in 2% Agarose-1™ TAE gels containing 0.5 µg/ml ethidium bromide.

Flow Cytometric Analysis of Cell Cycle.

The Caco-2 cells were grown in 6 well plates at a density of approximately $1.5\times10^5$ cells/well. Growth-arrested Caco-2 cells were preincubated with or without sorbinil 20 µM or carrier for 24 h and then stimulated with either 10 ng/ml bFGF or PDGF for another 24 h. The cells were then washed with PBS and harvested by trypsinization. Cellular DNA was stained with low and high salt solutions. Briefly, cells were resuspended in 250 µl of solution A, low salt stain, containing polytheleneglycol (30 mg/ml), propidium iodide (0.05 mg/ml), triton-x-100 (1 µl/ml), sodium citrate 4 mM, RNAse A 10 µg/ml and incubated at 37° C. for 20 min followed by the addition of 250 µl of solution B, high salt stain containing 400 mM NaCl instead of 4 mM sodium citrate in solution A, and incubated overnight at 4° C. Cell cycle analysis was performed with a minimum of 10,000 events per analysis by using FACScan flow cytometer (Becton, Dickinson and Co., San Jose, Calif., USA).

Measurement of Reactive Oxygen Species.

Caco-2 cells were plated in a 24-well plate at a density of $1.5\times10^4$ cells/well in DMEM and then serum-starved at 60-70% confluence in the absence and presence of 20 µM sorbinil or tolrestat for overnight in phenol redfree DMEM supplemented with 0.1% FBS. Cells were then pre-incubated for 30 min with the ROS-sensitive fluorophore 2',7'-dichlorofluorescein diacetate (DCFH-DA), which is taken up and oxidized to the fluorescent dichlorofluorescein by intracellular ROS. After incubation with DCFH-DA, the cells were exposed to FGF or PDGF 10 ng/ml for 60 min and fluorescence was measured with a CytoFluorII fluorescence plate reader (PerSeptive Biosystems, Inc., Framingham, Mass.) at excitation of 485 nm and emission of 528 nm.

Preparation of GS-Aldehyde Esters.

HNE was synthesized as described previously (14). The glutathione monoethyl-ester (GS-ester) obtained from Sigma was purified by HPLC using a reverse phase column (Ruef et al. (2000) *Arterioscler Thromb Vasc Biol* 20:1745-52) and the conjugate of GS-ester and FINE was made by incubating 1 µmol of [4-$^3$H]-HNE with 3-fold excess of GS-ester and 0.1 M potassium phosphate, pH 7.0, at 37° C. The reaction was followed by monitoring absorbance at 224 nm. Approximately 90% of FINE was conjugated with GSH over a period of 60 min. The GS-HNE-ester thus formed was purified by HPLC (Ruef et al. (2000) *Arterioscler Thromb Vasc Biol* 20:1745-52) and its concentration was calculated on the basis of radioactivity. For synthesis of GS-DHN-ester, 1 μmol of GS-HNE-ester was incubated with 1 unit of recombinant human AR and 0.1 mM NADPH in 0.1 M potassium phosphate, pH 7.0, at 37° C. The reaction was followed by monitoring the decrease in absorbance at 340 nm. More than 85% of the conjugate was reduced in 30 min. The enzyme was removed by ultrafiltration using an Amicon Centriprep-10, and GS-DHN-ester in the filtrate was purified on HPLC and confirmed by ESI/MS.

Western Blot Analysis.

To examine Cox-1, Cox-2, phospho PKC-β2 and GAPDH Western blot analyses were carried out as described earlier (Ramana et al. (2002) *J Biol Chem* 277(35):32063-70). Equal amounts of protein from cell extracts were subjected to 12% SDS-PAGE followed by transfer of proteins to nitrocellulose filters, probing with the indicated antibodies, and the antigen-antibody complex was detected by enhanced chemiluminescence (Pierce, Piscataway, N.J., USA).

Antisense Ablation of AR.

Caco-2 cells were grown to 50-60% confluence in DMEM supplemented with 10% FBS and washed four times with Opti-MEM, 60 min before the transfection with oligonucleotides (Ramana et al. (2002) *J Biol Chem* 277(35):32063-70). The cells were incubated with 2 μM AR antisense or scrambled control oligonucleotides using LipofectAMINE™ Plus (15 μg/ml) as the transfection reagent as suggested by the supplier. After 12 h, the medium was replaced with fresh DMEM (containing 10% FBS) for another 12 h followed by 24 h of incubation in serum-free DMEM (0.1% FBS) before growth factor stimulation. Changes in the expression of AR were estimated by Western blot analysis using anti-AR antibodies.

Statistical Analysis.

Data are presented as mean±SE and P values were determined by unpaired Student's t test. P values of <0.01 were considered significant.

Example 2

Effect of Ar Inhibition on TNF-α Generation in High Glucose

The effects of inhibiting PLC, NADPH oxidase and aldose reductase on the production of TNF-α in a culture medium (rat VSMC cells) are demonstrated. Growth-arrested VSMC in 5.5 mM glucose (NG) were preincubated for 1 h without or with apocyanin (25 μM), 0609 (100 μM), calphostin C (0.2 μM), N-acetyl cysteine (10 mM) and NF-KB inhibitor (18 μM) respectively, followed by the addition of 19.5 mM glucose, after which the cells were incubated for 12 and 24 hrs. Incubation with the PC-PLC inhibitor (calphostin C) markedly decreased TNF-α secretion. A similar decrease in TNF-α was observed in cells treated with the NADPH oxidase inhibitor apocyanin and the antioxidant N-acetylcysteine. Collectively, these observations support a mechanism in which high glucose increases TNF-α secretion by stimulating an intracellular signaling pathway that depends upon the activation of PLC and NADPH oxidase and the resultant change in the redox state of the cells.

That this mechanism requires aldose reductase is suggested by data that show either pharmacological inhibition of AR by treating cells with AR inhibitors sorbinil or tolrestat or antisense ablation of the AR gene prevents high glucose-induced TNF-α secretion. Treatment with AR inhibitors did not affect basal levels of TNF-α in media containing 5.5 mM glucose, mannitol, or 3-OMG. Moreover, high glucose-induced TNF-α production was not prevented in untransfected cells or cells incubated with the transfection medium or transfection medium containing scrambled oligonucleotides. These observations attest to the specificity of TNF-α generation on AR activity. Taken together, the signaling studies described above suggest that high glucose increases TNF-α secretion, by increasing aldose reductase and phospholipase C. These processes stimulate PKC and then NF-kB, which in turn increases transcription of the TNF-α gene.

Example 3

In Vitro and In Vivo Effects of Aldose Reductase Inhibition on Colon Cancer Cells Inhibition of AR Prevents PGE2 Production and Cox Activity in Colon Cancer Cells.

Figure 1B:
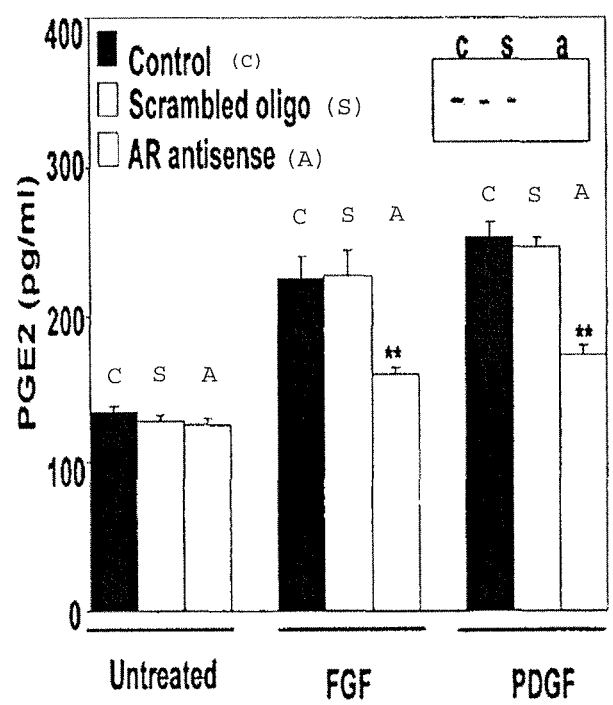

The growth factors are known to induce PGE2 production by activating inducible Cox-2 in colon cancer (Chen et al. (2005) *J Biol Chem* 280(16):16354-59), but the mechanism is not well understood. Inhibition of AR significantly (>90%) prevented the production of PGE2 by Caco-2 cells induced by bFGF and PDGF (FIG. 1A). However, sorbinil alone did not inhibit constitutive levels of PGE2. Since the non-specificity of AR inhibitors could not be rigorously excluded, parallel studies were performed by transfecting Caco-2 cells with antisense AR oligonucleotides that decreased AR protein expression by >95% (FIG. 1B, inset) and also the enzyme activity by >90% (data not shown). In contrast to the cells transfected with scrambled oligonucleotides, cells transfected with antisense AR displayed markedly attenuated PGE2 production upon stimulation with bFGF or PDGF (FIG. 1B). PGE2 generation in Cox-2 negative cells (HCT-116) by growth factors was nonsignificant (data not shown).

Figures 1C, 1D, 1E, 1F, 1G:
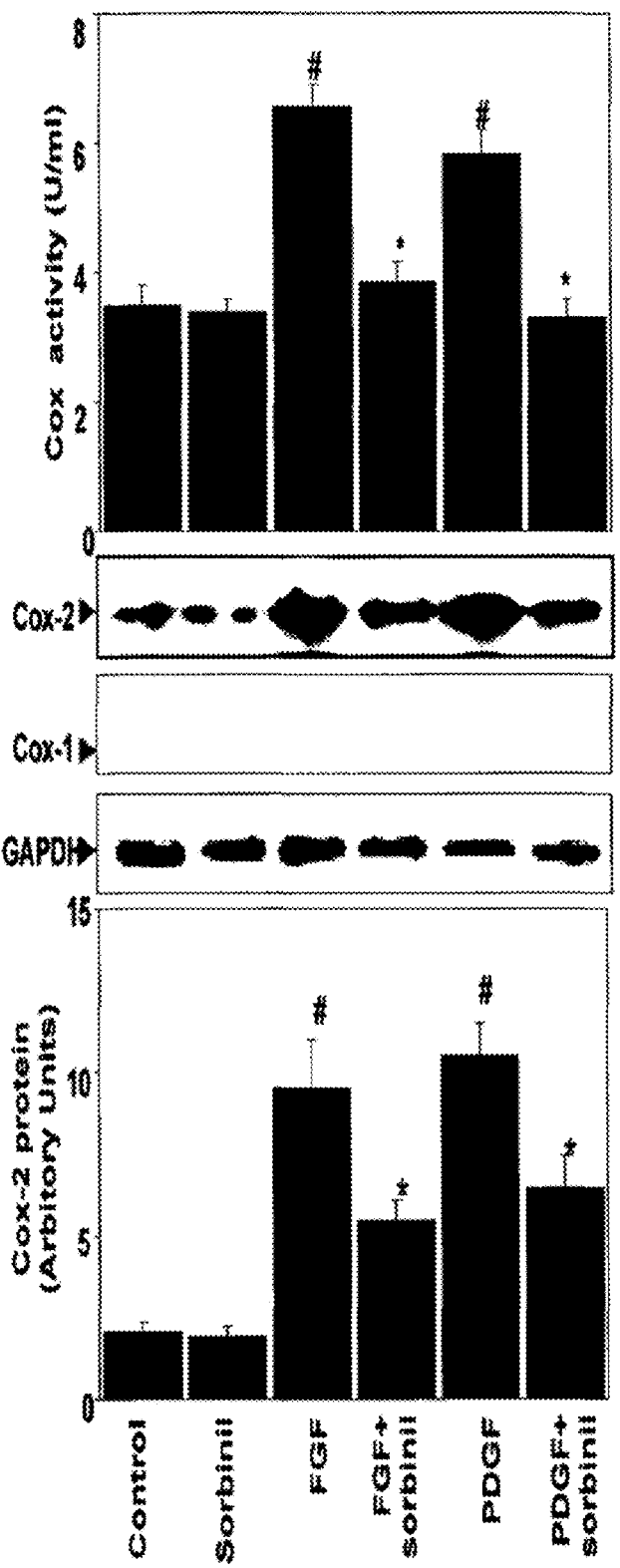

Since PGE2 is synthesized from its precursor arachidonic acid catalyzed by cyclooxygenases, whether or not inhibition of AR prevents growth factor-induced expression of Cox enzymes was examined. Treatment of Caco-2 cells with bFGF and PDGF significantly (60-80%) increased Cox activity (FIG. 1C). Pre-incubation with sorbinil abolished both bFGF and PDGF-induced Cox activity. Since Cox activity is contributed by two isozymes, constitutive Cox-1 and inducible Cox-2, the affect of AR inhibition on Cox-1 and Cox-2 isozymes was examined by Western blot analysis using specific antibodies. The levels of constitutive Cox-1 protein were not affected by growth factors or sorbinil (FIG. 1E), whereas Cox-2 protein significantly increased and was attenuated by sorbinil (FIGS. 1D, 1G).

Inhibition of AR Prevents Growth Factor-Induced NF-KB Activation in Colon Cancer Cells.

Figure 2A:
FIGS. 2A-2D illustrate that inhibition of AR prevents growth factor-induced Cox-2 mRNA expression and NF-kB in colon cancer cells. Growth-arrested Caco-2 cells were pre-incubated with sorbinil or carrier for 24 h followed by stimulation with of bFGF or PDGF for 3 h.
Figure 2B:
Figure 2C:
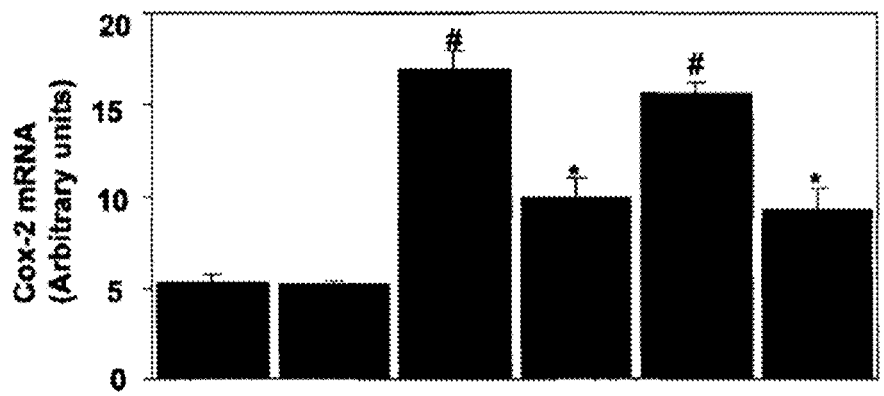
Figure 2D:
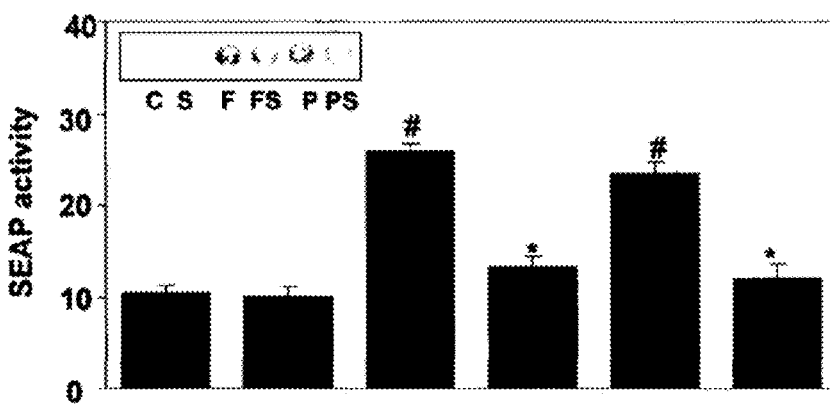
Figure 2E:
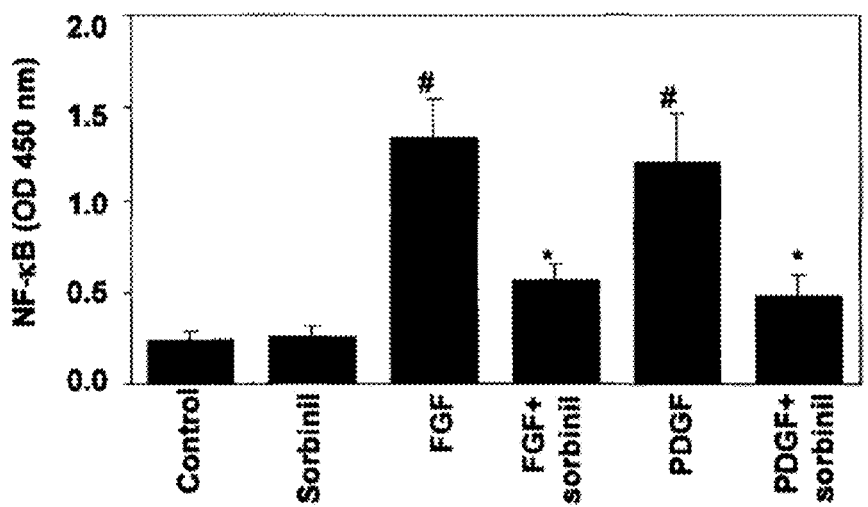
FIG. 2E shows NF-kB activity. Bars represent mean±S.E. (n=4); # $p<0.01$ as compared to control cells. * $p<0.01$ compared cells treated with growth factors.

The effect of AR inhibitors on growth factor-induced NF-kB activation was examined, because it is known that redox sensitive transcription factor NF-kB transcribes Cox-2 DNA (Chen et al. (2005) *J Biol Chem* 280(16):16354-359) and it has been demonstrated that AR inhibition prevents growth factors and cytokine-induced NF-kB activation (Ramana et al. (2002) *J Biol Chem* 277(35):32063-70). Treatment of caco-2 cells with bFGF or PDGF significantly (2-3 fold) increased the mRNA levels of Cox-2 and sorbinil prevented it by 55-65% (FIGS. 2A-2C) suggesting that AR could regulate the transcriptional activation of Cox-2 DNA. Both bFGF and PDGF significantly (~3 fold) induced NF-kB-dependent reporter (SEAP) activation in Caco-2 cells and sorbinil caused >60% inhibition (FIG. 2D). However, sorbinil alone did not affect the NF-kB-SEAP activity. Stimulation of Caco-2 cells with bFGF or PDGF resulted in a pronounced (~10 fold) activation of NF-kB DNA binding activity as determined by colorimetric, non-radioactive NF-kB p65 transcription assay method (FIG. 2E) and sorbinil caused >70% inhibition. These results validate previous measurements of NF-kB activity and substantiate that the specific activity observed in SEAP and colorimetric methods is due to NF-kB activation. It is contemplated that inhibition of AR prevents growth factor-induced activation of NF-kB in Caco-2 cells, which transcriptionally may activate Cox-2 expression.

Inhibition of AR Prevents Growth Factors-Induced PKC Activation in Colon Cancer Cells.

Figure 3E:
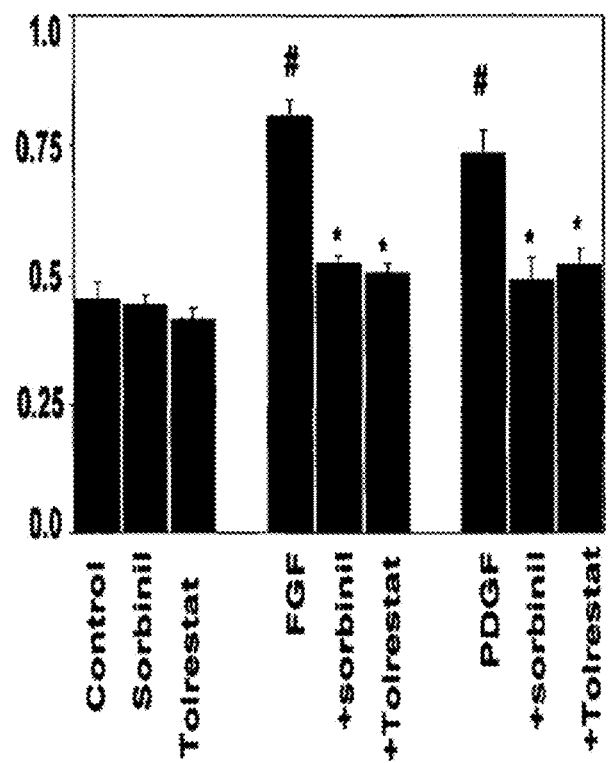

Since PKC is an upstream kinase for the activation of NF-kB and activation of PKC-$\beta 2$ has been implicated in colon carcinogenesis (Gokmen-Polar et al. (2001) Cancer Res 61(4):1375-1381), the effect of growth factors on total PKC activity in Caco-2 cells in the absence and presence of AR inhibitor was examined. Stimulation with growth factors led to a significant (~3 fold) increase in membrane-bound PKC activity (FIG. 3A) and sorbinil significantly prevented it. However, sorbinil by itself did not alter the total PKC activity in these cells. Both bFGF and PDGF activated PKC-$\beta 2$ in Caco-2 cells (FIGS. 3B, 3D). bFGF caused maximal PKC phosphorylation at 2 h whereas PDGF caused maximal phosphorylation at 1 h and increase in PKC-$\beta 2$ phosphorylation was significantly (>70%) attenuated by sorbinil.

Attenuation of Growth Factors-Induced Colon Cancer Cell Line Proliferation.

Figure 3F:
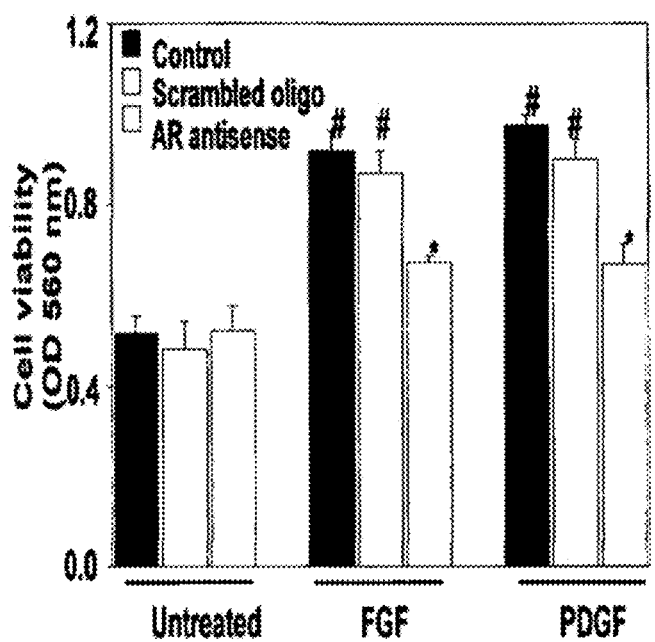

Since increased Cox-2 expression has been shown to facilitate colon cancer progression by stimulating cell proliferation and survival (Tsujii et al. (1998) Cell 93(5):705-716), we next examined the role of AR in growth factors-induced Caco-2 cell growth was examined. Treatment of Caco-2 cells with bFGF and PDGF for 24 h significantly (>40%) stimulated growth (FIG. 3E) which was significantly attenuated (>80%) by sorbinil or by antisense ablation of AR (FIG. 3F) indicating that AR is an obligatory mediator of growth factors-induced colon cancer cell proliferation.

AR Inhibition Affects S-Phase of Cell Cycle.

Figure 4:
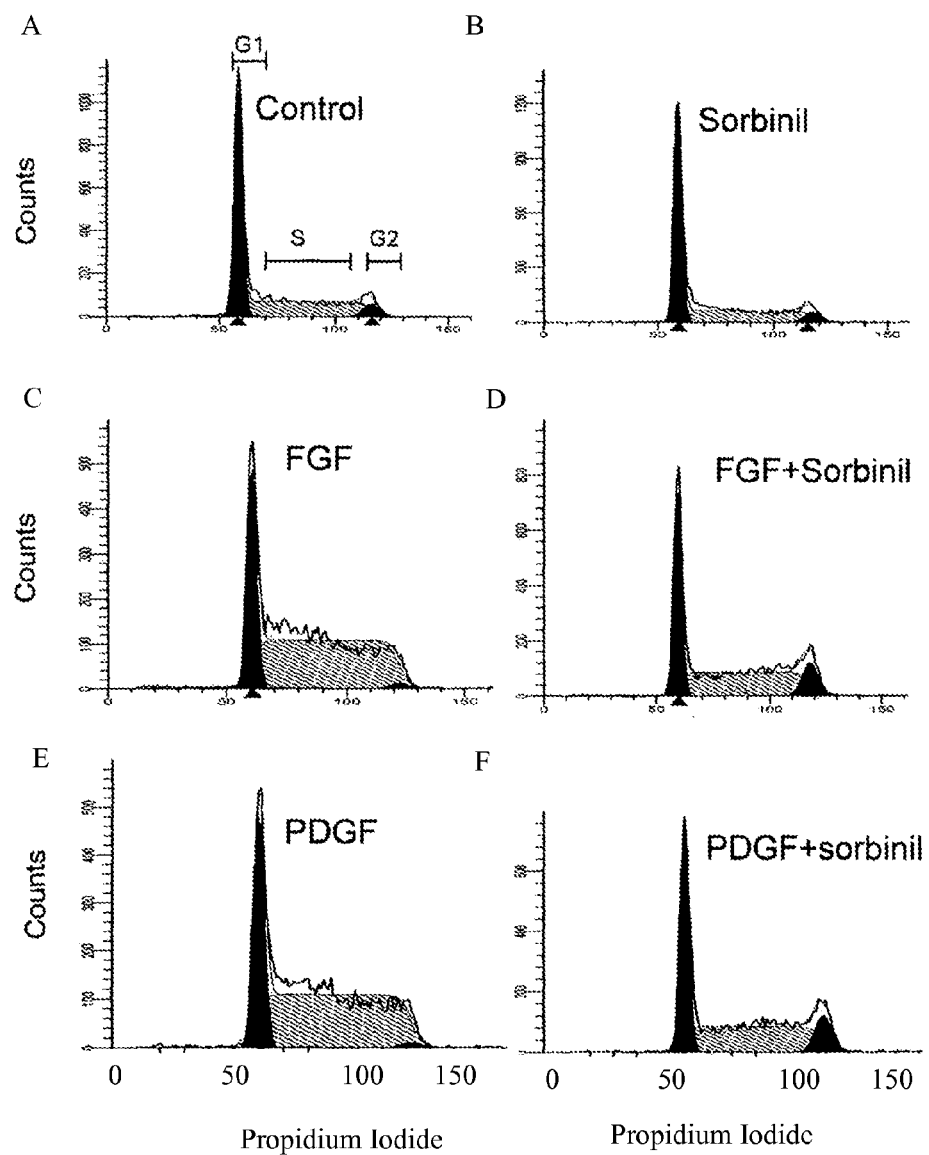
FIG. 4 illustrates that aldose reductase inhibition prevents growth factor-induced synthesis phase of cell cycle in colon cancer cells. Growth-arrested Caco-2 cells were pre-incubated with sorbinil or carrier for 24 h followed by stimulation with of bFGF or PDGF for 24 h and cell cycle analysis was performed by FACS. Table represents percentage of cells in the corresponding phase of cell cycle.

Since inhibition of AR attenuates growth factors-induced Caco-2 cell proliferation, the stage of cell cycle that is inhibited was determined. Treatment of cells with growth factors significantly induced synthetic (S)-phase of cell cycle (FIG. 4) suggesting that the cells were undergoing proliferation. Inhibition of AR prevented growth factor-induced accumulation of cells in S-phase and the cells accumulated at G2/M phase and G1 phase (FIG. 4), suggesting that AR inhibition prevents synthetic phase of cell cycle which is an important stage required for cell growth.

Attenuation of Growth Factors-Induced Upregulation of PGE2 Production by Inhibitors of Signaling Cascade for NF-KB Activation.

Figure 5A:
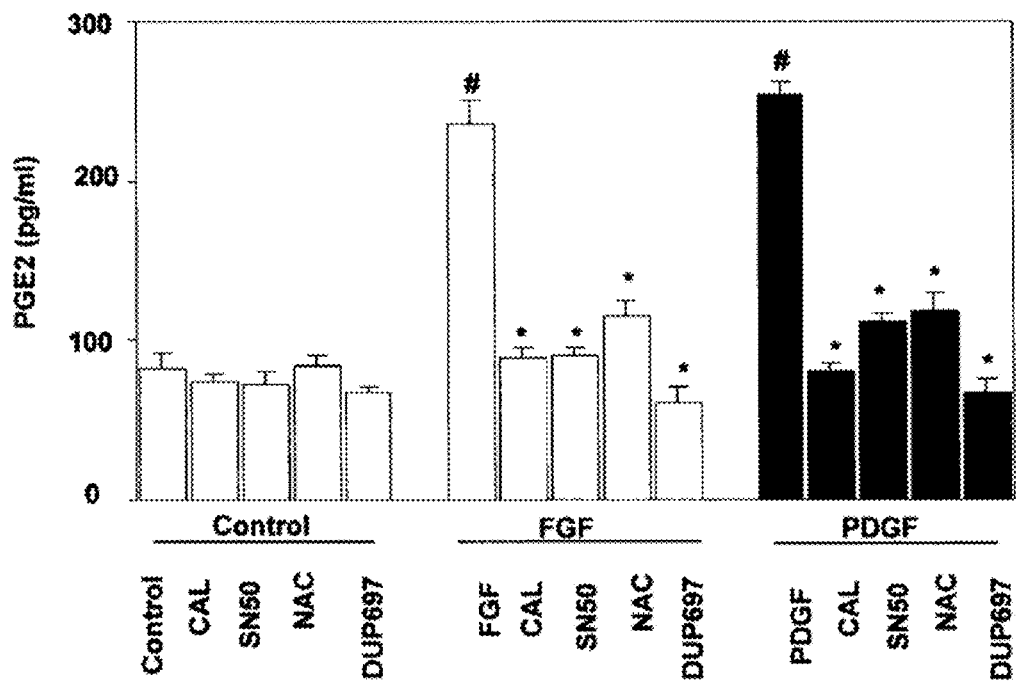
FIG. 5A-5B illustrate the effect of PKC, NF-kB and Cox-2 inhibitors and AR inhibitors on growth factor-induced PGE2 and ROS production, respectively in colon cancer cells. Growth-arrested Caco-2 cells were preincubated with PKC, NF-kB and Cox-2 inhibitors or ROS scavenger for 30 min (FIG. 5A) or AR inhibitors for 24 h (FIG. 5B). The growth-arrested Caco-2 cells were incubated further with bFGF or PDGF for 24 h (FIG. 5A) and 1 h (FIG. 5B). Bars represent mean±S.E. (n=4); # $p<0.001$ Vs. control cells and * $p<0.01$ Vs. cells treated with growth factors.
Figure 5B:
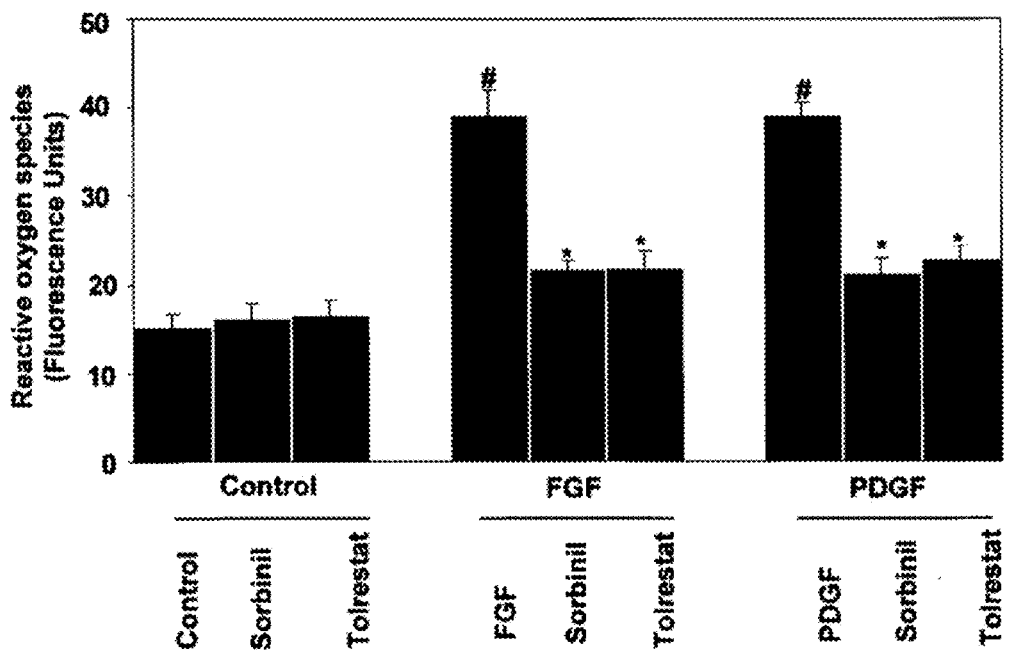

In order to understand the role of NF-kB in the growth factor-induced upregulation of PGE2, inhibitors of PKC (Calphostin c), Cox-2 (DUP697), reactive oxygen species scavenger (N-acetyl cysteine), and NF-kB (SN50) were utilized. Growth factors caused a pronounced increase in the production of PGE2 and preincubation of Caco-2 cell with the above inhibitors attenuated, indicating that signaling events that lead to activation of NF-kB and its dependent Cox-2 expression are involved in the production of PGE2 (FIG. 5A). Further, growth factors caused pronounced increase in ROS which was inhibited by sorbinil and tolrestat (FIG. 5B).

Effect of AR Inhibition on Lipid Aldehyde-Induced Signaling in Caco-2 Cells.

Figure 6A:
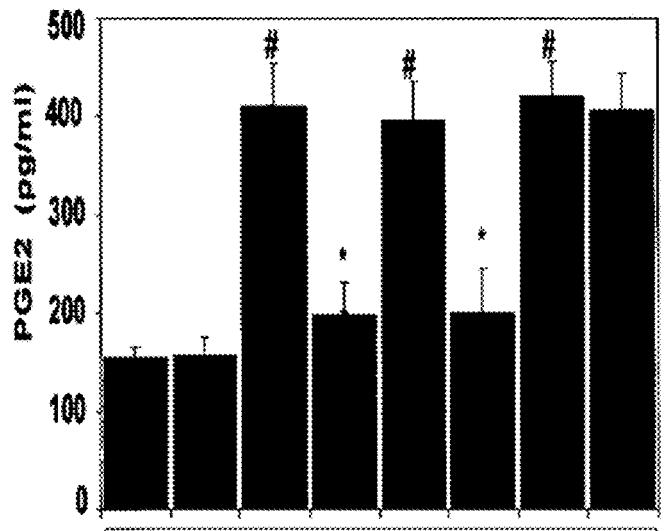
FIGS. 6A-6D illustrate the effect of AR-catalyzed reaction products on PGE2 and Cox-2 in colon cancer cells. The growth-arrested Caco-2 cells preincubated without or with sorbinil for 24 h were incubated with FINE, GSHNE- or GS-DHN-esters for 24 h.
Figure 6B:
Figure 6C:
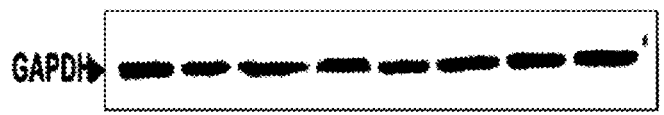
Figure 6D:
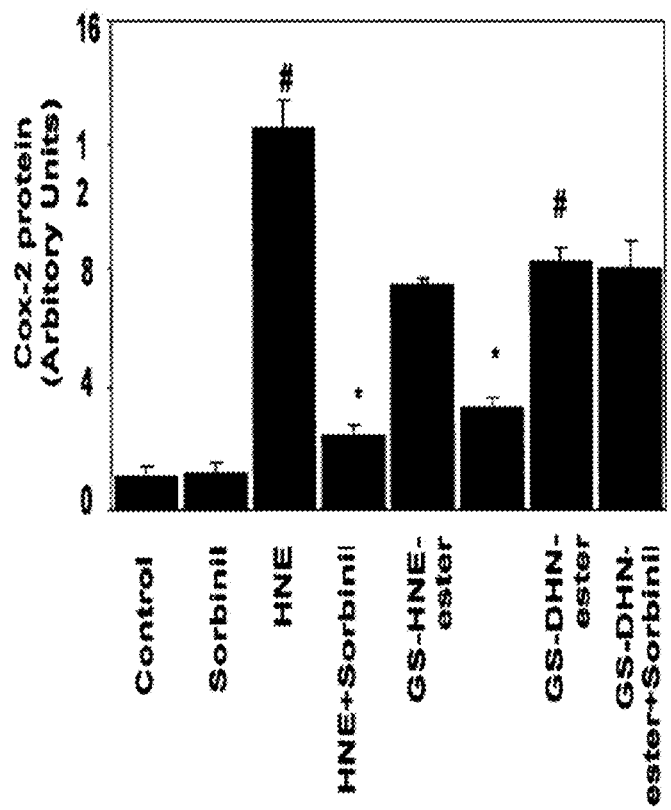

It has been demonstrated previously that AR is an excellent catalyst for the reduction of lipid peroxidation-derived aldehydes, such as FINE and their conjugates with glutathione to corresponding alcohols (Bhatnagar et al. (1992) Biochem. Med. Metab. Biol. 48:91-121; Ramana et al. (2000) Biochemistry 39:12172-80). Since, it is contemplated that AR inhibition or ablation prevents growth factor-induced expression of Cox-2 and production of PGE2, AR-catalyzed reduction of lipid aldehydes involvement in this mechanism was determined. Treatment of cells with FINE or cell permeable esters of GS-HNE or GS-DHN resulted in increased PGE2 production (FIG. 6A) and also Cox-2 expression (FIGS. 6B, 6D) Inhibition of AR by sorbinil significantly prevented the HNE and GS-HNE-induced Cox-2 expression and PGE2 production but had no effect on GS-DHN-induced expression of these inflammatory markers. These results indicate that growth factors-induced mitogenic signaling in colon cancer cells could be mediated by the reduced form of lipid aldehyde-glutathione conjugates catalyzed by AR.

Effect of Aldose Reductase siRNA on SW480 Xenografts.

Athymic nude nu/nu mice were obtained from Harlan, Indianapolis, Ind. All animal experiments were carried out in accordance with a protocol approved by the Institutional Animal Care and Use Committee (IACUC). Nine 20-weeks-old athymic nu/nu nude mice were divided into three groups of 3 animals (Group 1: treated with PBS; Group 2: treated with scrambled siRNA and Group 3: treated with aldose-reductase siRNA). An aliquot of $2 \times 10^6$ SW480 human colon adenocarcinoma cell suspensions in 100 μl PBS was injected subcutaneously into one flank of each nu/nu nude mouse. Animals were examined daily for signs of tumor growth. Treatment was administered when the tumor surface area exceeded 45 $mm^2$, i.e., day 25. Treatment consisted of 200 μg aldose-reductase siRNA in 100 μl PBS. Control groups were treated with 200 μg/100 μl scrambled siRNA, or diluent (PBS) alone. Mice were treated on days 1 and 14. Tumors were measured in two dimensions using calipers over 40 days.

Figure 7:
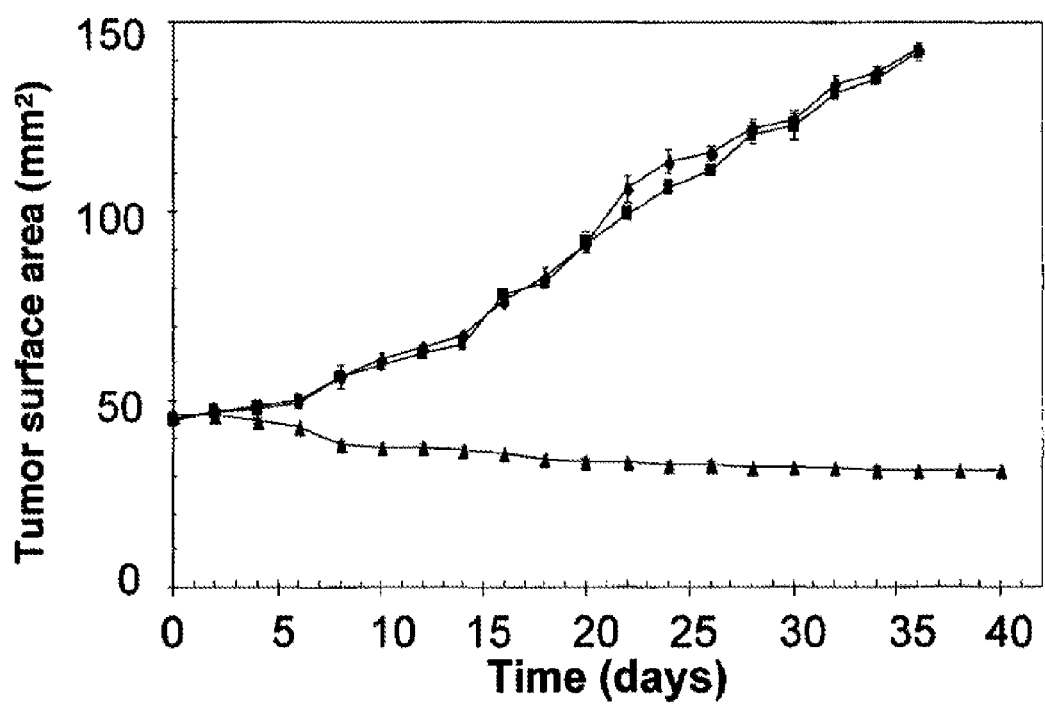
FIG. 7 illustrates the effect of AR siRNA on tumor size of SW480 xenografts. At different days tumors were measured in two dimensions using calipers.
Figure 8:
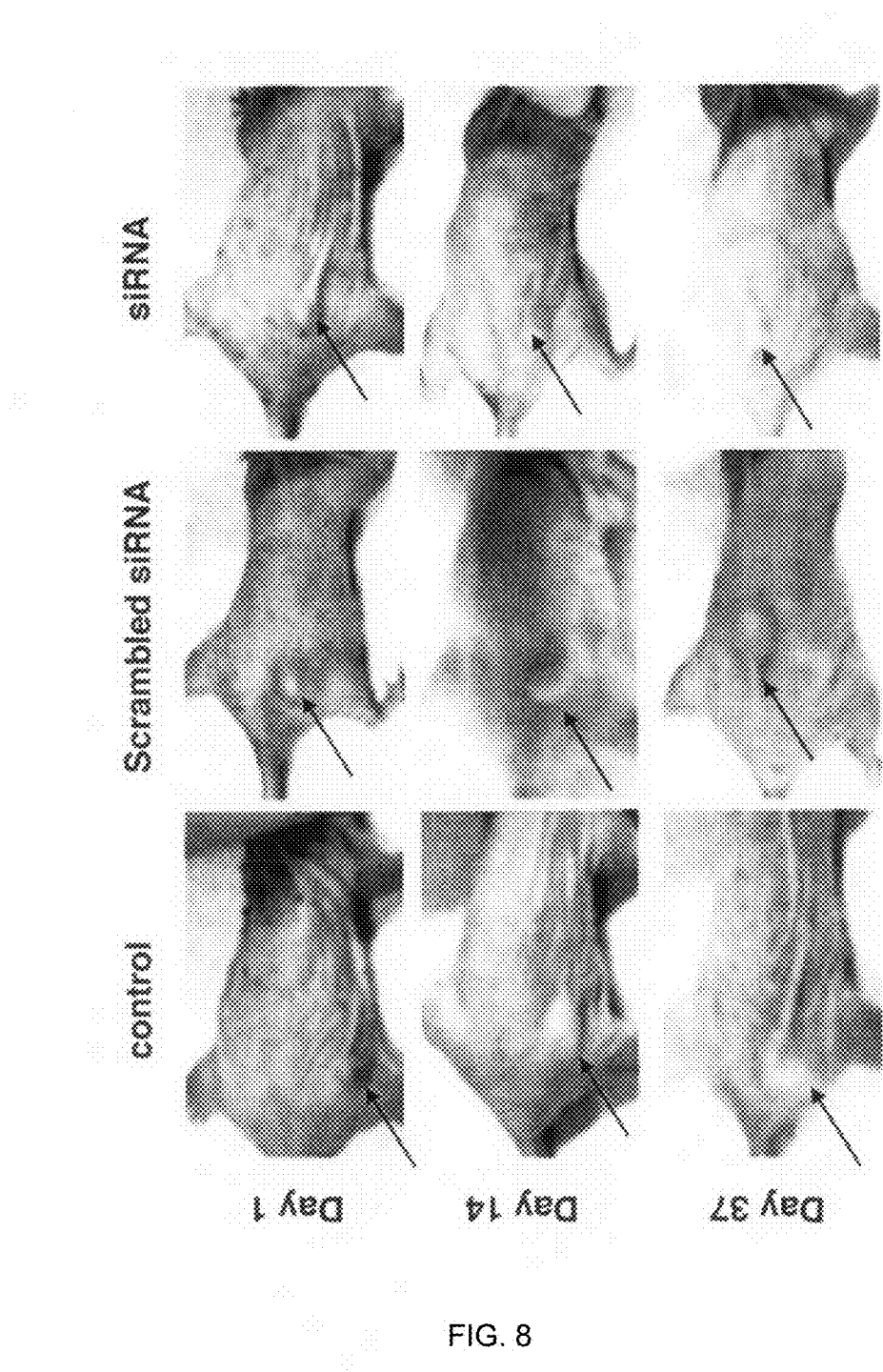
FIG. 8 Nine 20-weeks-old athymic nu/nu nude mice were divided into three groups of 3 animals (Group 1, circles: treated with PBS; Group 2, squares: treated with scrambled siRNA and Group 3, triangles: treated with aldose-reductase siRNA). An aliquot of $2\times10^6$ SW480 human colon adenocarcinoma cell suspension was injected into the mice and treatment was administered on the day the tumor surface area exceeded 45 mm$^2$ and 13 days later. At different days tumors were measured in two dimensions using calipers. Photographs of animals taken at 1, 14, and 37 days demonstrate the differences in tumor size.

Results presented in FIG. 7A clearly demonstrate that the tumor progression was completely arrested in the animals treated with an siRNA targeting aldose reductase (AR-siRNA), whereas uncontrolled growth was observed in the control as well as in scrambled siRNA treated mice. None of the treatments interfered with the normal weight gain of animals during the experiments. FIG. 7B are photographs of animals taken at 1, 14 and 37 days. These striking findings indicate that AR inhibition completely halts the colon cancer progression without interfering with the normal weight gain of the animals after its administration.

Any patents or publications mentioned in this specification are indicative of the levels of those skilled in the art to which the invention pertains. These patents and publications are herein incorporated by reference to the same extent as if each individual publication was specifically and individually incorporated by reference.

One skilled in the art will readily appreciate that the present invention is well adapted to carry out the objects and obtain the ends and advantages mentioned, as well as those inherent therein. It will be apparent to those skilled in the art that various modifications and variations can be made in practicing the present invention without departing from the spirit or scope of the invention. Changes therein and other uses will occur to those skilled in the art which are encompassed within the spirit of the invention as defined by the scope of the claims.

The invention claimed is:

1. A method of inhibiting colon cancer cell proliferation in a subject having colon cancer which consists of administering a pharmacologically effective amount of fidarestat which is a specific inhibitor of aldose reductase to the subject having colon cancer, wherein colon cancer cell proliferation in said subject is inhibited.

* * * * *